# (12) United States Patent
Koppolu et al.

(10) Patent No.: US 6,566,049 B2
(45) Date of Patent: May 20, 2003

(54) ENZYMATIC APPROACH FOR ANALYTICAL METHOD DEVELOPMENT

(76) Inventors: Ajoy P. K. Koppolu, 2244 Vine St., #204, Lincoln, NE (US) 68503; Lakshmi Koppolu, 2244 Vine St., #204, Lincoln, NE (US) 68503

( * ) Notice: Subject to any disclaimer, the term of this patent is extended or adjusted under 35 U.S.C. 154(b) by 0 days.

(21) Appl. No.: 09/821,296

(22) Filed: Mar. 29, 2001

(65) Prior Publication Data

US 2002/0001796 A1 Jan. 3, 2002

Related U.S. Application Data

(60) Provisional application No. 60/192,951, filed on Mar. 29, 2000.

(51) Int. Cl.$^7$ .............................. C12Q 1/00; C12P 1/00; C12N 11/00; C12N 9/00
(52) U.S. Cl. ............................. 435/4; 435/41; 435/174; 435/183
(58) Field of Search .............................. 435/4, 174, 41, 435/183

(56) References Cited

U.S. PATENT DOCUMENTS

| | | | |
|---|---|---|---|
| 4,447,527 A | 5/1984 | Monte et al. | 435/188 |
| 5,362,630 A | 11/1994 | You | 435/25 |
| 5,441,872 A | 8/1995 | Tulley | 435/25 |
| 6,015,683 A | * | 1/2000 | Schaeffer et al. | 435/24 |

OTHER PUBLICATIONS

Fox et al; "PGPUB–Document–No.: 20020039723)"; Apr. 4, 2002.*
USP 24/NF 19,1999, p. 18, 44, 162–164 Rockville, MD, USA.
Patricia Cunniff, Official Methods of Analysis of AOAC International, 1998, p.23–28, vol. 2, MD, USA.
A.C. Moffat, Clarke's Isolation and Identification of Drugs, 1986, p. 153, The Pharmaceutical Press, $2^{nd}$ edn.
British Pharmacopeia, The Stationary office, 1999, p. 132, vol. 1, London, U.K.
S.I. West, Industrial Enzymology, 1996, p. 63, $2^{nd}$ Edition, MacMillan Press Limited, London, U.K.

* cited by examiner

Primary Examiner—Louise N. Leary

(57) ABSTRACT

A novel enzymatic approach for analytical method development is disclosed. A process wherein enzymes replace commonly used reagents/chemicals in a method/procedure. This approach increases the speed of analysis, reduces the usage of reagents/solvents, decreases the quantities of wastes generated, reduces the overall cost of drug testing/analysis in pharmaceutical or other related industries. The approach can be used to assay or analyze an active/inactive ingredient present in a solid, liquid, or semi-solid dosage forms of a drug.

11 Claims, No Drawings

ENZYMATIC APPROACH FOR ANALYTICAL METHOD DEVELOPMENT

This application claims the benefit of Provisional application Ser. No. 60/192,951, filed Mar. 29, 2000.

BACKGROUND OF THE INVENTION

The present invention relates generally to a novel approach to quantify/measure/assay an active or inactive ingredient in a drug or a formulation either in solid, semi-solid, or liquid dosage forms. The approach described herein utilizes enzymes that would lead to many advantages when compared to current/conventional non-enzymatic analytical methods/procedures development. This invention also applies to various analytical methods used in related industries like biotechnology, bioprocesssing, and chemical industries.

Analytical method development is carried out on a daily basis in many industries including pharmaceutical industries. Methods or procedures are developed for assays, identification, or estimation of the quantity, purity, or contaminants of a component or components of a product. Drug analysis or assay of actives/inactives in a formulation is performed regularly in pharmaceutical industries. These methods are used to test the stability or the integrity of a finished product and the reasons for the analysis of drugs include: to estimate the uniformity of the drug preparation to establish or release a bulk manufactured product; to estimate the shelf life or stability of the product; to check the quantity of active/inactive remaining in a drug/formulation after a certain period of time. These testing or analysis are carried out on solid, semi-solid, and liquid dosage forms.

The methods, though routine, are performed by a trained group of analysts solely dedicated for this task. These approaches use reactive compounds, organic solvents, or water and some of the common steps of a procedure are physico-chemical in nature such as titration, extraction, chromatography, or in general separation techniques. Though this approach works well, certain features are not desirable. Therefore, there is a need to improve or completely eliminate these negative features. The drawbacks are: use of large quantities of solvents/reagents/water, sequence of numerous analytical steps in analysis, disposal of large quantities of solvents/reagents, a large lab space to work and for storage of chemicals, disposal fee for solvents, more analysts' time or man-hours requirement, to name a few. Conventional drug/pharmaceutical formulation analyses have other negative features apart from the above mentioned. The requirement of additional steps in a method would lead to more analysts' errors. This certainly would lead to an extra amount of man-hours, resources (chemicals, reagents, solvents, water), exposure to hazards, and more importantly other projects accumulate thus affecting the deadlines and economics of drug manufacture itself. This becomes more clear with a detailed description of examples for acetaminophen and aspirin, comparing prior art and the present invention. Some of the examples where present invention can be applicable include: naproxen, ibuprofen, docusate sodium, hydrocortisone, pseudoephedrine, etc. to name a few.

There are numerous biochemicals and chemicals in nature that can be produced naturally or synthetically which are also biodegradable. These degrade over a period of time with the help of non-biological environmental factors such as air, pn rain, and sun. Apart from these factors, microorganisms like bacteria and fungi, also play a major role in degrading or destroying many of these biochemicals or chemicals that are disposed of into the environment.

Microorganisms accomplish this task with the help of enzymes present in them. Enzymes are an integral part of a microorganism's mechanism to act on a substance or a suitable substrate to degrade it for food or nutrition. The enzymes are either intracellular or extracellular to microorganisms. The substrate or a chemical in the environment can be degraded outside or inside of a microorganism. Enzymes are involved in either situations. Some of the examples of enzymes are amylases, lipases, oxidases, dehydrogenases, cerulases, and hydroxylases.

Enzymes are highly specific in their reactivities toward chemicals. They combine or react with chemicals using the sites present on them. Besides specificity, enzymes react very quickly in comparison to a reaction between any two chemicals. Enzymes are powerful biocatalysts and they can be used in much smaller quantities to get the same kind of reactivity that is obtained with non-enzymatic chemical compounds. Therefore, a small amount of enzyme is capable of reacting with large amounts of chemicals at a faster rate. In other words, high specific nature of enzymes help them in converting or reducing a reactant to a product quickly. Enzymes are also reusable and easily biodegradable. The reaction product can be monitored and measured with the help of the product's absorbance. Usually, the concentration of the product formed is directly proportional to absorbance (a linear relationship) and can be quantified with a spectrophotometer or a calorimeter.

Enzymes are also used in the field of immunology, where qualitative and quantitative analyses are performed on biologically active substances such as blood, saliva, or urine. The present disclosure is primarily aimed at non-biologically active substances such as drugs, formulations, or chemicals that have to be quantitatively assayed in various industries.

The present invention eliminates or reduces to a great extent most of the above problems through the use of enzymes. This approach has many decisive advantages which include simplicity, accuracy, less time consuming, cheaper, and non or less polluting.

SUMMARY OF THE INVENTION

It is a primary object of the present invention to provide a novel approach to quantify or measure an active or inactive ingredient in a drug/formulation through an enzymatic route. It is a further object of the present invention that by following this approach one can realize many advantages over current analytical/method development procedures namely:

a) faster analysis b) lower chemicals/reagents usage and cost c) fewer man-hours d) smaller lab space e) fewer health/safety hazards f) cheaper approach g) less strain on the environment due to fewer pollutants

DETAILED DESCRIPTION OF THE INVENTION

The examples given below illustrate the benefits of enzymatic approach. The cumbersome methods that are being followed can be replaced by a simpler, faster, cheaper method. Since the drug testing is routinely performed throughout the world, one or more positive features of enzymatic approach could save millions of dollars in disposal requirements, reagents cost, and total testing time. Saving testing time could also mean more testing of batches in a short amount of time and a faster release of products into the market at a lower price. A reduction in harmful and dangerous reagents and solvents usage would reduce the exposure amount for an analyst and enhances the working conditions in the laboratories.

Anyone skilled in the art of method development would appreciate the potential benefits of the enzymatic approach. The scope of the approach is not just limited to the analysis of a single active or inactive ingredient in one step, but unlimited to many active or inactive ingredients testing simultaneously with the help of one or more enzymes.

The method is also amenable to automation. Once the analytical method is validated the amount of chemicals required, man-hours saved, and the overall method ruggedness play vital roles in cutting down the cost of product or raw material testing. This means the overall product cost will decrease and in return the consumers can buy drugs/pharmaceuticals for a lower price. Further, the introduction of enzymatic approach can lead to exciting new avenues in the field of analytical method development. Some examples such as simultaneous testing of two or more ingredients, information on the interplay between enzyme-active-excipient, and the application of the latter in medicine and health, etc.

The following two examples describe the differences between the current or conventional approach in drug and pharmaceutical industries and the enzymatic approach of the present invention. First example describes the testing of a drug component acetaminophen and the second example illustrates the testing performed on aspirin, which is also a drug component. It is clear from both examples that the advantages of the present disclosure over the conventional approach are not only useful but essential in saving time, keeping the environment clean, and accelerating the drug testing process.

EXAMPLE 1

For Acetaminophen

| Conventional Approach | Enzymatic approach |
|---|---|
| I. Sample preparation: | I. Sample preparation: |
| 1. weigh and powder 20 tables | 1. weigh and powder 20 tablets |
| 2. take equivalent to 100 mg acetaminophen in 200 mL flask | 2. take equivalent to 100 mg acetaminophen in 200 mL flask |
| 3. use 200 mL of 3:1 water/methanol | 3. use 200 mL. of 3:1 water/methanol |
| 4. shake for 10 min | 4. shake for 10 min |
| 5. sonicate for 5 min | 5. sonicate for 5 min |
| 6. transfer 5 mL from step 3 to 250 mL flask and dilute to volume | 6. take an aliquot and filter through 0.5 µm filter |
| 7. filter a portion through 0.5 µm filter | 7. add enzyme preparation with or without a coupling agent and incubate for 5–15 min |
| 8. inject 10 µL of sample and standard preparations into HPLC | 8. measure absorbance at suitable wavelength using a desk-top spectrophotometer |
| II. Standard preparation: | |
| 1. dissolve about 100 mg of acetaminophen in 100 mL of | 9. calculate or estimate |

-continued

| Conventional Approach | Enzymatic approach |
|---|---|
| mobile phase | acetaminophen amount using a calibrated graph |
| III. Mobile phase: | |
| 1. prepare 500 mL of water and methanol (3:1) mixture | II. Enzyme preparation: |
| IV. HPLC analysis: | 1. can be prepared in a buffer having known concentration of an enzyme or enzymes |
| 1. wash column with any mixture of water/methanol for at least 15 min | 2. a calibration graph can be constructed for varying concentrations of acetaminophen and time |
| 2. wash column with mobile phase for 10 min and equilibrate to get a steady base line | 3. this is done only once and can be used repeatedly for any number of batches |
| 3. inject standard and sample preparations and elute analytes from | III. Mobile phase: |
| the column | 1. not required |
| 4. perform calculations to estimate the amount/assay | IV. HPLC analysis: |
| 5. wash column with water/ | 1. not required |
| | V. Chemicals used: |
| methanol mixture for about 15 min before storing | 1. water: 200 mL |
| V. Chemicals used: | 2. enzyme(s): 1 mL of enzyme solution or less depending |
| 1. methanol: 300 mL | on the enzyme concentration |
| 2. water: 950 mL | VI. Disposal burden: |
| 3. acetaminophen: 100 mg | 1. none; enzymes are easily biodegradable |
| VI. Disposal burden: | |
| 1. 300 mL methanol or | VII. Health/safety hazards: |
| 1250 mL (total) | 1. none |
| VII. Health/safety hazards: | VIII. Reagents to be purchased: |
| 1. exposure to methanol | 1. water, enzymes (a small cost) |
| 2. handling of explosive solvent | |
| VIII. Reagents to be purchased: | |
| 1. methanol, water, acetaminophen | |

EXAMPLE 2

For Aspirin

| Conventional Approach | Enzymatic Approach |
|---|---|
| I. Sample preparation: | I. Sample preparation: |
| 1. weigh and crush 20 tablets and transfer equivalent to 100 mg aspirin | 1. see under sample preparation for Aspirin |
| | II. Diluting solution: |
| 2. add 20 mL diluting solution, mix and centrifuge | 1. none |
| | III. Standard preparation: |
| 3. dilute 1 part in 9 parts with diluting solution | 1. none; only one standard preparation is needed for many batches of product testing |
| II. Diluting solution: | |
| 1. Acetonitrile: | IV. Enzyme preparation: |
| formic acid = 99:1 | 1. suitable enzyme or enzymes |

-continued

| Conventional Approach | Enzymatic Approach |
|---|---|
| III. Standard preparation: | can be used in very small volume to cleave or react with aspirin |
| 1. mix 100 mg aspirin in 200 mL of diluting solution | |
| IV. Mobile phase: | V. HPLC assay/mobile phase: |
| 1. 2 g sodium 1-heptane-sulfonate in 850 mL water and 150 mL acetonitrile | 1. none |
| | VI. Reagents: |
| V. HPLC analysis: | 1. none |
| | VII. Disposal: |
| 1. see example 1 | 1. none; enzymes are easily biodegradable |
| VI. Reagents: | |
| 1. acetonitrile: 550 mL | VIII. Safety/health hazards: |
| 2. formic acid: 4 mL | 1. none |
| 3. aspirin: 100 mg | |
| VII. Disposal: | |
| 1. acetonitrile: 550 mL | |
| 2. formic acid: 4 mL | |
| 3. water: 850 mL | |
| VIII. Safety/health hazards: | |
| 1. acetonitrile/formic acid handling | |

What is claimed is:

1. A process using one or more enzymes in analytical method and/or procedure development for the purpose of either:
   a) assay and/or analysis of one or more active ingredients;
   b) assay and/or analysis of one or more inactive ingredients;
   c) assay and/or analysis of one or more active and inactive ingredients;
   in a drug or a formulation comprising the steps of:
      i. selecting at least one enzyme and at least one drug or formulation;
      ii. reacting the ingredient in said drug or formulation with said enzyme in the presence or absence of other reactants;
      iii. analyzing or observing the enzymatic reaction product;
      iv. collecting data that relates to the enzymatic reaction product;
      v. correlating the data obtained with the presence of a quantifiable amount of the said active and/or inactive ingredient.

2. A process using one or more enzymes in analytical method and/or procedure development for the purpose of either:
   a) assay and/or analysis of one or more active ingredients;
   b) assay and/or analysis of one or more inactive ingredients;
   c) assay and/or analysis of one or more active and inactive ingredients;
   in a drug or a formulation comprising the steps of:
      i. selecting at least one enzyme and at least one drug or formulation;
      ii. preparing the said enzyme and/or drug or formulation for reacting;
      iii. reacting the ingredient in said drug or formulation with said enzyme in the presence or absence of other reactants;
      iv. analyzing or observing the enzymatic reaction product;
      v. collecting data that relates to the enzymatic reaction product;
      vi. correlating the data obtained with the presence of a quantifiable amount of the said active and/or inactive ingredient.

3. A process of claim 1 or 2 where an active and/or inactive ingredient is the one that makes up a small part or the whole of the drug or formulation.

4. A process of claim 1 or 2 where a drug or a formulation is a solid, semi-solid, liquid, or gas dosage form.

5. A process of claim 1 or 2 where a drug or formulation is a combination of a solid, liquid or gaseous states of matter that result in a dosage form that cannot be classified as a solid, semi-solid, liquid, or a gas dosage form.

6. A process of claim 1 or 2 where an enzyme is a chemical or a biocatalyst of microbial or synthetic origin either manufactured or naturally available.

7. A process of claim 1 or 2 in which the method or procedure is characterized by, in comparison to conventional techniques, omission of one or more steps used in drug testing and/or analysis leading to improved pharmaceutical efficiency.

8. A process of claim 1 or 2 in which the method or procedure is characterized by, in comparison to conventional techniques, modification of one or more steps used in drug testing and/or analysis leading to improved pharmaceutical efficiency.

9. A process of claim 1 or 2 in which the method or procedure is characterized by, in comparison to conventional techniques, inclusion of one or more enzymatic assay and/or analysis steps leading to improved pharmaceutical efficiency.

10. A process of claim 1 or 2 in which the method or procedure is characterized by, in comparison to conventional techniques, omission of one or more steps and/or modification of one or more steps and inclusion of one or more enzymatic assay and/or analysis steps leading to improved pharmaceutical efficiency.

11. A process of claim 1 or 2 in which the method or procedure is characterized by, in comparison to conventional techniques, reduced use of solvents and/or reagents, decreased analysis time, reduced pollutants, reduced waste generation, and increased pharmaceutical efficiency.

* * * * *